(12) United States Patent
Henriksen et al.

(10) Patent No.: US 6,943,151 B2
(45) Date of Patent: Sep. 13, 2005

(54) METHOD OF INHIBITING BONE RESORPTION AND/OR PROMOTING BONE FORMATION USING GLP-2 AND RELATED COMPOUNDS

(75) Inventors: Dennis B. Henriksen, Alleroed (DK); Jens J. Holst, Hellerup (DK)

(73) Assignee: Sanos Bioscience A/S (DK)

(*) Notice: Subject to any disclaimer, the term of this patent is extended or adjusted under 35 U.S.C. 154(b) by 0 days.

(21) Appl. No.: 10/391,460

(22) Filed: Mar. 18, 2003

(65) Prior Publication Data

US 2004/0082507 A1 Apr. 29, 2004

Related U.S. Application Data

(63) Continuation of application No. PCT/EP01/10714, filed on Sep. 17, 2001.

(30) Foreign Application Priority Data

Sep. 18, 2000 (GB) .............................................. 0022844
Dec. 7, 2000 (GB) .............................................. 0029920

(51) Int. Cl.[7] .............................................. A61K 38/00
(52) U.S. Cl. .......................................... 514/21; 514/12
(58) Field of Search .................... 514/12, 21; 530/308, 530/324

(56) References Cited

U.S. PATENT DOCUMENTS 6,770,620 B2    8/2004    Henriksen ...................... 514/2

FOREIGN PATENT DOCUMENTS

| EP | 0 955 314 A2 | 11/1999 |
|---|---|---|
| WO | WO 96/32414 | 10/1996 |
| WO | WO 97/31943 | 9/1997 |
| WO | WO 98/24813 | 6/1998 |
| WO | WO 98/52600 | 11/1998 |
| WO | WO 99/14239 | 3/1999 |
| WO | WO 00/34331 | 6/2000 |
| WO | WO 00/34332 | 6/2000 |
| WO | WO 01/41779 A2 | 6/2001 |
| WO | WO 01/87322 A2 | 11/2001 |
| WO | WO 01/98331 A2 | 12/2001 |
| WO | WO 02/10195 A2 | 2/2002 |
| WO | WO 02/24214 A2 | 3/2002 |
| WO | WO 02/066062 A2 | 8/2002 |

OTHER PUBLICATIONS

Haderslev et al. Does Short–Term Administration of Glucagon–Like Peptide Type 2 . . . Gastroenterology. Apr. 2001, vol. 120, No. 5, Supplement 1, p. A–314, Abstract 1619.*
Francis, Roger M., "Bisphosphonates in the Treatment of Osteoporosis in 1997: A Review"; Current Therapeutic Research, vol. 58, pp. 656–678, No. 10, Oct. 1997.
Haderslev, K. V. et al., "Short–term Administration of Gluagon–like Peptide-2. Effects on Bone Mineral Density and Markers of Bone Turnover in Short–Bowel Patients with No Colon"; Taylor & Francis Healthsciences, pp. 392–398. Scandinavian J. of Gastroenterology, vol. 37, No. 4 (Apr. 2002).

* cited by examiner

Primary Examiner—Jeffrey Edwin Russel
(74) Attorney, Agent, or Firm—Edwards & Angell, LLP.; Robert L. Buchanan; Gregory B. Butler

(57) ABSTRACT

Disclosed are methods of inhibiting bone resorption and/or promoting bone formation using GLP-2 and related Compounds. The invention has a wide spectrum of important uses including hyperparathyroidism, Paget's disease, hypercalcemia of malignancy, osteolytic lesions produced by bone metastasis, bone loss due to immobilisation or sex hormone deficiency, osteomalacia, hyperostosis and osteopetrosis.

22 Claims, 5 Drawing Sheets

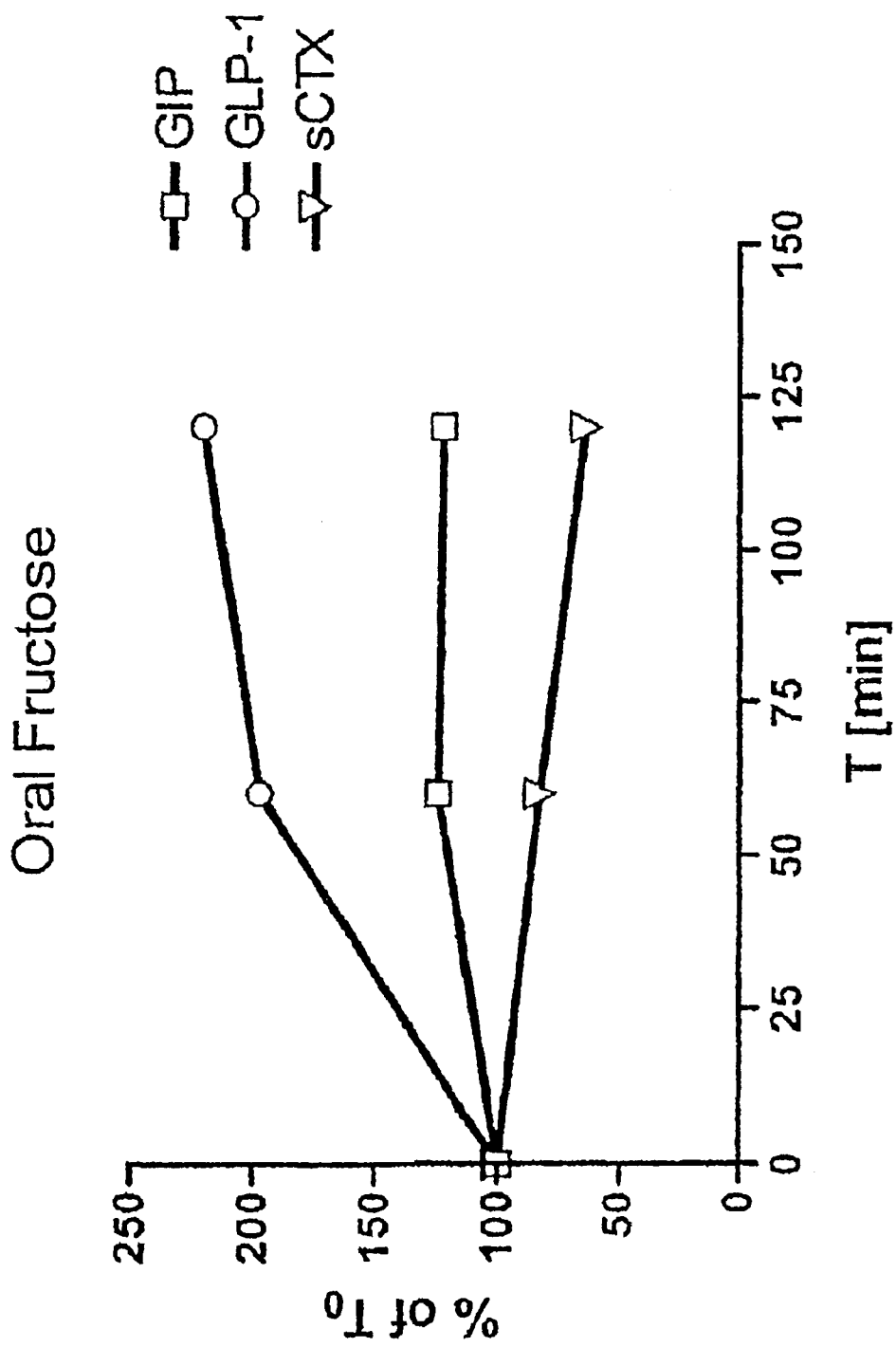

METHOD OF INHIBITING BONE RESORPTION AND/OR PROMOTING BONE FORMATION USING GLP-2 AND RELATED COMPOUNDS

The present application is a continuation of PCT International Application Number PCT/EP01/10714 as filed on 17 Sep. 2001, which application claims priority to GB 0022844.5 as filed on 18 Sep. 2000 and GB 0029920.6 as filed on 7 Dec. 2000. The disclosures of the PCT/EP01/08056, GB0022844.5 and GB 0029920.6 applications are incorporated herein by reference.

FIELD OF THE INVENTION

This invention relates to the use of glucagon-like peptide-1(GLP-1) as well as inducers, analogues and derivatives of GLP-1, and of glucagon-like peptide-2 (GLP-2) and inducers analogues and derivatives of GLP-2, in methods and compositions, in particular pharmaceutical formulations, for the treatment of diseases wherein bone resorption and/or insufficient bone formation is a factor, such as osteoporosis.

BACKGROUND OF THE INVENTION

Glucagon-like peptide-1 (GLP-1) and glucagon-like peptide-2 (GLP-2) are fragments of the proglucagon molecule and the proglucagon molecule has a sequence of 160 amino acids. Proglucagon originates from preproglucagon which is synthesised in the L-cells in the distal ileum, in the pancreas and in the brain. Processing of preproglucagon to give GLP-1 and GLP-2 occurs mainly in the L-cells.

The amino acid sequence of the proglucagon fragment 72–117 is given i.e. by Bell, G. I. et al. (Nature 304 368–371 (1983)). The proglucagon fragment 78–108 is commonly referred to as GLP-1 (7–37). In analogy with this, the proglucagon fragment 72–108 is in the present text also referred to as GLP-1 (1–37).

The proglucagon fragment of GLP-1 (7–36)amide is the naturally occurring form in humans and is usually referred to as GLP-1. Gutniak, M., N Engl. J. Med., 326:1316–22 (1992).

A simple system is used to describe fragments and analogues of the GLP-1 related peptide. Thus, for example, Gly8-GLP-1 (7–37) designates a fragment of GLP-1 formally derived from GLP-1 by replacing the amino acid residue in position 8 (Ala) by Gly.

Variants of GLP-1 (7–37) and analogues thereof have been disclosed, for example, Gln9-GLP-1 (7–37), D-Gln9-GLP-1 (7–37), acetyl-Lys9-GLP-1 (7–37), Thr16-Lys18-GLP-1 (7–37), Lys18-GLP-1 (7–37) and the like, and derivatives thereof including, for example, acid addition salts, carboxylate salts, lower alkyl esters, and amides (see e.g. WO 91/11457).

Glucagon-like peptide-1 (GLP-1) is known to stimulate insulin secretion and inhibit glucagon secretion and thereby lowers blood glucose, Andreasen, J. J. et al. (Digestion 55 221–228 (1994)). Generally, the various disclosed forms of GLP-1 are known to stimulate insulin secretion and cAMP formation (see e.g., Mojsov, S. (Int. J. Peptide Protein Research 40 333–343 (1992))).

Glucagon-like peptide-2 (GLP-2) is a 33 amino acid peptide fragment of proglucagon corresponding to the sequence of the proglucagon fragment 126–158. GLP-2 shows remarkable homology in terms of amino acid sequence to glucagon and glucagon-like peptide-1 (GLP-1). Further, different mammalian forms of GLP-2 are highly conserved. For example, the human GLP-2 (hGLP-2)and the degu (a south American rodent) GLP-2 differ from rat GLP-2 (rGLP-2) by one and three amino acids respectively.

Various vertebrate forms of GLP-2 have been reported by many authors including Buhl et al., J. Biol. Chem., 1988, 263 (18):8621, Nishi and Steiner, Mol. Endocrinol., 1990, 4:1192–8, and Irwin and Wong, Mol. Endocrinol., 1995, 9 (3):267–77. The sequences reported by these authors are incorporated by reference.

When given exogenously, GLP-2 can produce a marked increase in the proliferation of small intestinal epithelium of the test mice, apparently with no undesirable side effects (Drucker et al., 1996, PNAS:USA, 93 7911–7916). Moreover, GLP-2 has also been shown to increase D-glucose maximal transport rate across the intestinal basolateral membrane (Cheeseman and Tseng, 1996, American Journal of Physiology 271 G477–G482).

Osteoporosis is the most common bone disease in humans. It is a serious and frequent disease, which occurs worldwide. The single most important risk factor for osteoporosis is oestrogen deficiency, and it is estimated that up to one third of postmenopausal women will be affected if left untreated, Schlemmer, A. et al., Eur. J. Endocrinol. 140:332–337 (1999). A primary event leading to osteoporotic bone loss is the increase in bone turnover associated with menopause. The acute increase in bone resorption seen with the decline in endogenous oestrogen production is followed by a coupled, but less accentuated increase in bone formation. This net imbalance between resorption and formation results in bone loss thereby increasing fracture risk.

Other diseases and metabolic disorders which result in loss of bone structure are for instance, hyperparathyroidism, Paget's disease, hypercalcemia of malignancy, osteolytic lesions produced by bone metastasis, bone loss due to immobilisation or sex hormone deficiency, Behcet's disease, osteomalacia, hyperostosis and osteopetrosis.

Surprisingly, it has now been discovered that administered GLP-1 peptide or GLP-2 peptide have an effect on loss of bone mass and/or insufficient bone formation in humans. Based on these observations it is now possible to provide a medicament and a method for the prophylaxis or treatment of diseases or disorders wherein bone resorption and/or insufficient bone formation is a factor, such as osteoporosis.

SUMMARY OF THE INVENTION

In one aspect, the present invention relates to the use of a composition comprising a glucagon-like peptide-1 (GLP-1) or an analogue or derivative thereof, and/or a glucagon-like peptide-2 (GLP-2) or an analogue or derivative thereof, to inhibit bone resorption and/or to promote bone formation.

In the present text, the designation "an analogue" is used to designate a peptide wherein one or more amino acid residues of the parent peptide have been substituted by another amino acid residue and/or wherein one or more amino acid residues of the parent peptide have been deleted and/or wherein one or more amino acid residues have been added to the parent peptide.

The term 'analogue' further includes mimetics so the said peptides which bind to the receptors for said peptides and activate said receptor to produce an output messenger or signal equivalent in kind to that produced upon binding of GLP-1 or GLP-2 respectively. Such analogues may be adapted to resist degradation in the body to an extent greater than GLP-1 or GLP-2 and so may have a longer half life or may be orally administerable. Such analogues will include pseudo-peptides modelled on GLP-1 or GLP-2 in which one or more amino acid residues have been substituted with structurally similar but peptidase resistant amino acid mimicking moieties.

In the present text, the designation "amino acid residue" designates the residue of an amino acid which can be coded for by the genetic code, via a triplet ("codon") of nucleotides. In the present text, the peptides to which the invention relates are referred to collectively as "GLP-1 peptides" and similarly collectively as "GLP-2 peptides'.

'Derivatives' referred to herein include for example, acid addition salts, carboxylate salts, lower alkyl (e.g. $C_1$–$C_6$, more preferably $C_1$–$C_3$, esters and amides. Also included are substances formed by chemical modification of GLP-2 peptide which retain the bone resorption decreasing and/or bone formation increasing properties of GLP-2 at an equivalent or increased level.

In another aspect, the present invention relates to the use of a composition comprising a glucagon-like peptide-1 (GLP-1) or an analogue or derivative thereof, and/or a glucagon-like peptide-2 (GLP-2) or an analogue or derivative thereof, in the preparation of a medicament for the treatment of a disease wherein bone resorption and/or insufficient bone formation is a factor.

Preferably the disease is osteoporosis.

In a third aspect, the present invention relates to a method of inhibiting bone resorption and/or promoting bone formation, comprising, administering to a subject a compound selected from the group consisting of GLP-1, GLP-2, GLP-1 analogues, GLP-2 analogues, GLP-1 derivatives, GLP-2 derivatives, agonists of the GLP-1 or the GLP-2 receptor, agonists of the GLP-1 or the GLP-2 signal transduction cascade, compounds that stimulate synthesis of endogenous GLP-1 or GLP-2, compounds that stimulate release of endogenous GLP-1 or GLP-2, and pharmaceutically acceptable derivatives such as esters, amides or salts thereof.

A preferred embodiment of the present invention relates to a method wherein the composition is selected from the group consisting of GLP-2, GLP-2 analogues, GLP-2 derivatives, and pharmaceutically acceptable salts, esters or amides thereof.

In a further preferred embodiment, the present invention relates to a method wherein the composition is administered orally.

Another aspect of the present invention relates to a method of prophylactically treating a subject at risk of developing a disease wherein bone resorption and/or insufficient bone formation is a factor, the method comprising the steps of a) identifying a subject at risk of developing such a disease; and b) administering to the subject an amount of a compound selected from the group consisting of GLP-1, GLP-2, GLP-1 analogues, GLP-2 analogues, GLP-1 derivatives, GLP-2 derivatives, agonists of the GLP-1 or the GLP-2 receptor, agonists of the GLP-1 or the GLP-2 signal transduction cascade, compounds that stimulate synthesis of endogenous GLP-1 or GLP-2, compounds that stimulate release of endogenous GLP-1 or GLP-2, and pharmaceutically acceptable salts, amides or esters thereof, effective to inhibit onset of said disease.

In a preferred embodiment, the present invention relates to a method of treatment wherein the disease is osteoporosis.

In a further preferred embodiment, the present invention relates to a method wherein the subject is a human.

Another aspect of the present invention relates to a composition used for inhibition of bone resorption and/or the promotion of bone formation, said composition comprising a compound selected from the group consisting of GLP-1, GLP-2, GLP-1 analogues, GLP-2 analogues, GLP-1 derivatives, GLP-2 derivatives, agonists of the GLP-1 or the GLP-2 receptor, agonists of the GLP-1 or the GLP-2 signal transduction cascade, compounds that stimulate synthesis of endogenous GLP-1 or GLP-2, compounds that stimulate release of endogenous GLP-1 or GLP-2, and pharmaceutically acceptable salts thereof.

Preferably, the compound is an orally effective analogue or derivative. Preferably, where such a compound is on which stimulates endogenous production or release of GLP-1 or GLP-2, it is not nutritionally effective or is not found as a component of foodstuffs.

In a further embodiment, the present invention relates to a pharmaceutical composition for use in the therapeutic or prophylactic treatment of a disease wherein bone resorption or insufficient bone formation is a factor, said composition comprising a compound selected from the group consisting of GLP-1, GLP-2, GLP-1 analogues, GLP-2 analogues, GLP-1 derivatives, GLP-2 derivatives, agonists of the GLP-1 or the GLP-2 receptor, agonists of the GLP-1 or the GLP-2 signal transduction cascade, compounds that stimulate synthesis of endogenous GLP-1 or GLP-2, compounds that stimulate release of endogenous GLP-1 or GLP-2, and pharmaceutically acceptable salts thereof.

BRIEF DESCRIPTION OF THE DRAWINGS

The present invention is further illustrated with reference to the appended drawings wherein FIG. 1 shows in graphs A, B and C results obtained in Examples 1–3. FIG. 1A shows the levels of GLP-1, GIP and S-CTX over a 2–3 hours period responding to oral fructose. GIP (Glucose-dependent Insulinotropic Polypeptide) is an incretin that stimulates insulin secretion directly in a glucose-dependent manner. S-CTX is a serum C-telopeptide fragment of collagen type I degradation.

DETAILED DESCRIPTION OF THE INVENTION

Figure 1B:
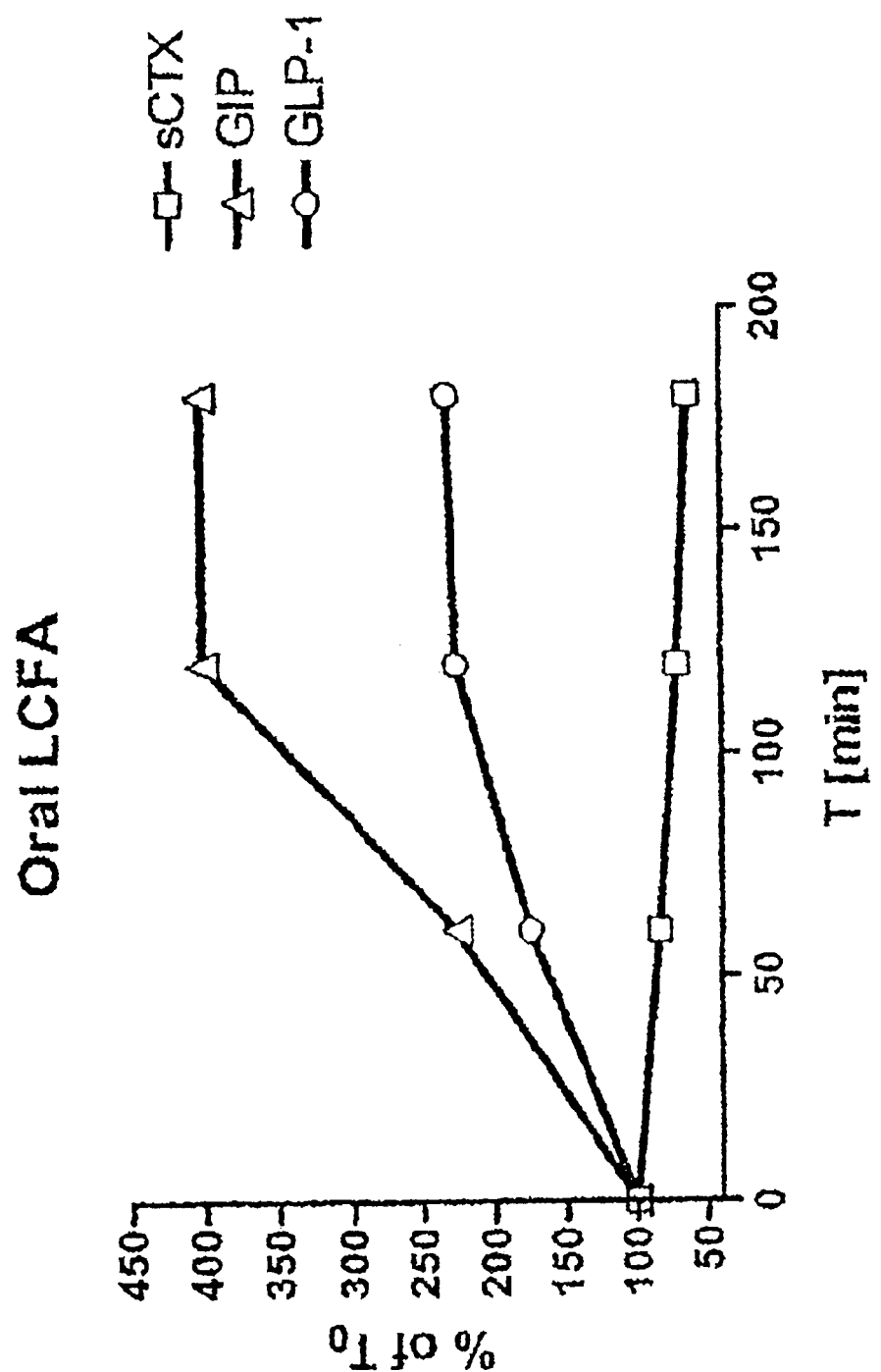
FIG. 1B shows the levels of GLP-1, GIP and S-CTX over a 2–3 hours period responding to oral long chain fatty acid, LCFA

This invention comprises the use of glucagon-like peptide-1 (GLP-1), analogues and derivatives of GLP-1, glucagon-like peptide-2 (GLP-2), analogues and derivatives of GLP-2, for the treatment of diseases wherein bone resorption and/or insufficient bone formation is a factor, such as osteoporosis.

Diseases and metabolic disorders which result in loss of bone structure would benefit from such a treatment. For instance, hyperparathyroidism, Paget's disease, hypercalcemia of malignancy, osteolytic lesions produced by bone metastasis, bone loss due to immobilisation or sex hormone deficiency, Behcet's disease, osteomalacia, hyperostosis and osteopetrosis, could benefit from administering a GLP-1 peptide and/or a GLP-2 peptide.

It is well known to use biochemical markers to be able to biochemically assess the level of bone resorption and formation in order to evaluate a risk for a future fracture. However, there is a considerable circadian variation with a peak in the early morning and the lowest level in the afternoon. This is usually taken care of by fasting during measurement.

This variation is independent of gender, age and stage of osteoporosis although an elevated baseline level is seen in postmenopausal women. It is also dependent of physical activity, thus 3 days of bed-rest does not change the variation in pre-menopausal women. Circadian variation in plasma cortisol as a possible factor has been studied.

Neither cortisol-insufficient individuals substituted intermittently with cortisol to eliminate circadian variation nor cortisol-clamp studies in healthy postmenopausal women demonstrated any influence on circadian variation in bone resorption. PTH-clamp studies in pre- and postmenopausal women had shown that the circadian variation in bone turnover is also independent of serum PTH concentration. Recently a study in pre-menopausal women demonstrated that circadian variation in bone resorption measured by urinary excretion of C-telopeptide fragments of collagen type 1 degradation was significantly diminished during fasting, Schlemmer, A. et al., Eur. J. Endocrinol. 140:332–337 (1999).

The biochemical mechanisms underlying the circadian variation in bone resorption remain poorly understood.

An association between insulin levels after OGTT/oral glucose and bone mass in healthy, postmenopausal women has been observed, Reid, I. R. et al., The American Physiological Society E655–E659 (1993). Moreover, baseline data from the Rotterdam Study demonstrated that this association was present in both elderly men and women, but were reduced after correction for BMI, Stolk, R. P. et al., Bone 6:545–549 (1996). In this cohort, previously non-vertebral fracture was associated with a lower post-load insulin level. Preliminary follow up data from the study suggest that baseline post-load insulin levels corrected for BMI and bone mass are associated with a reduced risk of incident non-vertebral fractures, Hendrikse, J. et al., ASBMR-IBMS Second Joint Meeting S501. Finally, data from OGTT/oral glucose in 19.000 Swedish men and women without known diabetes suggest that a high post load S-glucose in non-diabetic individuals is associated with a lowered risk of hip fracture, Johnell, O. et al., ASBMR-IBMS Second Joint Meeting S170. Thus, there appears to be an association between insulin response and bone mass as well as subsequent fracture risk. This association may partially be explained by an influence of insulin upon bone resorption. The possibility of such a relationship is supported by the recent demonstration of insulin receptors on osteoclast-like cells, Thomas, D. M. et al., Bone 23:181–186 (1993) and on osteoblast, Thomas, D. M. et al., J. Bone Miner. Res. 11:1312–1320 (1996).

The skeleton is (among other things) a reservoir of nutrients, including minerals such as calcium and phosphate. This reservoir is usually well protected but in situations of insufficient access to nutrients giving rise to a decreasing extra cellular concentration of these nutrients the stores of these in the skeleton can be mobilised. Likewise, in situations of sufficient access to nutrients the metabolic machinery of the body is set to preserve the stores.

For the skeleton such mobilisation of the stores can be achieved by stimulating osteoclastic bone resorption, and likewise resorption can be decreased when dietary availability of nutrients increases.

Such regulation of bone metabolism has previously been demonstrated for dietary intake of calcium. It has recently been observed that also oral glucose can decrease bone resorption, with a fully expressed decrease within 2 hours, GB Patent Application No. 0007492.2.

This response is independent of gender and age. A comparable effect was demonstrated for protein. Thus, dietary intake may regulate bone resorption, partially via insulin secretion as shown by insulin stimulation test.

It is stated in GB Patent Application No. 0007492.2 that oral intake of nutrient produces a short term fall in the rate of bone resorption. Furthermore, administration of insulin in an insulin tolerance test (ITT) similarly produces a short term fall in the measured rate of bone resorption.

The nutrients that can inhibit bone resorption may be a sugar, a protein, or a fatty acid, or a triglyceride, or a mineral. Fatty acids used were preferably long chain fatty acids.

It had been shown and described that-drugs on the market for treating osteoporosis have undesirable side effects. It is concluded by Graham, D. Y. et al., Aliment Pharmacol Ther 4:515–9 (1999) that alendronate (Fosamax) causes gastric ulceration. Furthermore, it is stated that the common used hormone replacement therapy (HRT) increases the risk of breast cancer, Persson, I. et al., Int. J. Cancer 72 (5):758–25 61 (1997).

Therefore, there is a need for a medicament for the treatment of diseases wherein bone resorption and/or insufficient bone formation and/or insufficient bone formation is a factor, such as osteoporosis that do not show the undesirable side effects mentioned above.

According to the present invention, it is now surprisingly shown that the fragments of proglucagon produced in the intestine have a role in the inhibition of bone resorption and also a role in promoting bone formation (an anabolic bone effect).

The proglucagon expressed in the α-cells of the endocrine pancreas and in the enteroendocrine L-cells of the intestine arises from the transcription of a single gene and the translation of identical mRNAs in these two tissues. Biologic diversity in the expression of the proglucagon gene occurs at the level of a remarkably tissue-specific alternative post-translational processing, resulting in the formation of the bioactive peptide glucagon in the pancreas and the reciprocal insulin-stimulating GLP-1 in the intestine.

The glucagon and GLP sequences in intestine and pancreas, respectively, are retained as unprocessed proglucagon fragments: enteroglucagon (glicentin) in the intestine and the major proglucagon fragment in the pancreas, Habener, J. F., Diabetes Mellitus 68–78 (1996).

Glicentin or proglucagon fragment 1–69 is cleaved in the pancreas to GRPP (glicentin-related pancreatic polypeptide) and glucagon, whereas the major proglucagon fragment 72–158 is cleaved (processed) in the intestine to GLP-1 (proglucagon fragment 78–107) and GLP-2 (proglucagon fragment 126–158) fragments.

It is notable that the alternative processing of the identical proglucagon in the intestine and pancreas give rise to peptides whose physiologic functions are opposed. GLP-1 of the intestine is an anabolic hormone that among other things facilitates stimulation of insulin secretion and glucose uptake during feeding, whereas glucagon from pancreas is the most important catabolic hormone that acts during periods of fasting to break down glycogen (and thereby to increase glucose output by the liver), skeletal muscle, and adipose tissue.

The proteolytic cleavage of the proglucagon in the intestine is part of a complicated process. At least four peptides of GLP-1 result from the processing: two peptides of 37 and 36 amino acids, GLP-1 (1–37) and GLP-1 (1–36)amide; and two aminoterminally truncated isopeptides, GLP-1 (7–37) and GLP-1 (7–36) amide. Only the two truncated GLP-1s have insulinotropic activities. Previously, no biologic activities have been found for either of the amino-terminally extended forms of GLP-1. Both isopeptides of GLP-1, GLP-1 (7–37) and GLP-1 (7–36)amide, have insulinotropic potencies in all systems in which they have been studied so far, including humans, Habener, J. F., Diabetes Mellitus 68–78 (1996). In humans the predominating product is GLP-1 (7–36)amide, and very little is produced of the other forms.

GLP-1 has been proven to be a potent glucose-dependent insulinotropic peptide distinct from GIP. GIP (Gastric Inhibitory Polypeptide which has been changed to Glucose-dependent Insulinotropic Polypeptide), is an incretin that stimulates insulin secretion directly in a glucose-dependent manner.

The amino acid sequence of GIP was determined in 1981 by Jörnvall et al, FEBS Lett 123:205 (1981). The combination of the two hormones GIP and GLP-1, however, appears to constitute most if not all of the relevant hormonal component of the incretin effect, Nauck, M. A. et al., J Clin Endocrinol Metab 1993; 76 (4):912–917.

The intestinal processing of proglucagon also gives rise to GLP-2 corresponding to proglucagon 126–158. Only a single form is known in humans, Hartmann B et al., Peptides 2000; 21 (1):73–80.

GLP-2 seems to share some of the effect of GLP-1 on gastro-intestinal motility and secretion, Wojdemann, M. et al., J Clin Endocrinol Metab 1999; 84 (7):2513–2517 and Wo demann, M. et al, Scand J Gastroenterol 1998; 33 (8):828–832, but has no direct effect on the pancreatic islets. In contrast GLP-2 has trophic effect on the intestinal mucosa, and may act physiologically as a growth factor involved in adaptive responses of the gut to surgery or nutritional variation, Drucker, D. J. et al., Proc Natl Acad Sci USA 1996; 93 (15):7911–7916 and Thulesen, J. et al., Gut. In press. It inhibits apoptosis and cause epithelial proliferation in the small intestine, Tsai, C. H. et al., Am J Physiol 1997; 273 (1 Pt 1):E77–E84, and may be used clinically to treat patients with the short bowel syndrome Jeppesen, P. B. et al., Gastroenterology. In press. It acts via a G-protein coupled receptor which is expressed in several regions of the body, particularly in the intestinal mucosa, Munroe, D. G. et al., Proc Natl Acad Sci USA 1999; 96 (4):1569–1573.

Compounds which can be useful as GLP-1 peptides according to the present invention are described in International Patent Application No. WO 87/06941 which relates to a peptide fragment which comprises GLP-1 (7–37) and functional derivatives thereof and to its use as an insulinotropic agent.

Further GLP-1 analogues are described in International Patent Application No. WO 90/11296 which relates to peptide fragments which comprise GLP-1 (7–36) and functional derivatives thereof and have an insulinotropic activity which exceeds the insulinotropic activity of GLP-1 (1–36) or GLP-1 (1–37) and to their use as insulinotropic agents.

International Patent Application No. WO 91/11457 discloses analogues of the active GLP-1 peptides 7–34, 7–35, 7–36, and 7–37, which can also be useful as GLP-1 peptides according to the present invention.

Derivatives of naturally-occurring GLP-1 molecules are those peptides which are obtained by fragmenting a naturally-occurring sequence,.or are synthesised based upon a knowledge of the sequence of the naturally-occurring amino acid sequence of the genetic material (DNA or RNA) which encodes this sequence. The term "derivatives" also includes chemical modification of natural or unnatural GLP-1 or GLP-2 molecules. Processes for preparing these derivatives are well known to organic and peptide chemists of ordinary skill (see, e.g. WO 91/11457).

As used herein the terms "GLP-1 receptor agonist" and "GLP-2 receptor agonist" mean any molecule which on binding to the GLP-1 receptor, respectively the GLP-2 receptor result in activation of the GLP-1 receptor, respectively the GLP-2 receptor, and include for example GLP-1, GLP-2 or peptidic analogues of GLP-1 and GLP-2. Recently it has been demonstrated that the GLP-1 receptor and the GLP-2 receptor are G-protein coupled receptors. Thus, methods commonly used in this field to identify G-protein coupled receptor agonists may be useful applied to the GLP-1 receptor respectively the GLP-2 receptor. One useful methodology for assessing. compounds for GLP-2 receptor agonist activity is disclosed in U.S. Pat. No. 6,077,949.

The mode of action of GLP-1 and of GLP-2 is not yet fully elucidated. It may be that one or both operates through a signal transduction cascade in which there may be active constituents either upstream or downstream or both from the GLP peptide. According to the invention, it is permissible to intervene at any point in such a cascade to produce a reduction in the rate of bone resorption and/or to promote the rate of bone formation by the mechanism of the cascade. This may involve stimulating the synthesis or release of endogenous GLP peptide or administering or triggering endogenous synthesis or release of another compound active in the cascade downstream from the GLP peptide, e.g. one produced in response to the GLP peptide binding to a receptor.

Bone formation and growth is a complex process consisting of changes in bone diameter and shape. This process occurs through the sequential activation of two cell types: osteoclasts and osteoblasts. Osteoblasts are of mesenchymal origin derived from fibroblast colony forming units, as are chondrocytes, muscle cells and adipocytes. Osteoblasts are capable of secreting a number of factors (such as interleukins-6 and 11; MCS-F and GM-CSF) that can affect the development of osteoclasts. Osteoclasts develop from granulocye-macrophage colony forming units and their development is modulated by a variety of factors, including interleukins 1, 3, 6 and 11. Recently, considerable interest has focused on interleukin-6 because its production from osteoblasts is stimulated by PTH and vitamin D and because of its possible involvement in several diseases including primary hyperparathyroidism, multiple myeloma, rheumatoid arthritis, Paget's disease and hypogonadal osteoprosis. Interleukin-6 production from osteoblasts is regulated by sex-hormones (androgens and estrogens) which act on the Il-6 promotor. The role of Il-6 (in contrast to Il-11) in normal osteoclastic function is unclear but in certain pathologic states the Il-6 receptor is upregulated and Il-6 may then exert is effect. In bone cells derived from hypogonadal mice gp80, gp130 and Il-6 mRNA are all increased compared to normal cells. Thus, it is possible that Il-6 plays an important role in the accelerated bone loss associated with postmenopausal osteoporosis.

It follows that GLP-1 and GLP-2 may play an important role in the regulation of both skeletal growth in the child, and skeletal remodelling in the adult. GLP may act on receptors present in bone derived cells and stimulation of these cells with GLP leads to an increase in intracellular calcium concentration and cellular cAMP content, resulting in increased type I collagen synthesis and inhibition of PTH-stimulated bone resorption.

The invention includes the use of other fragments obtainable from the cleavage of the major proglucagon fragment which also have GLP-like activity.

The term "subject" includes a human or other mammal and including livestock and pets.

Administration may be via any route known to be effective by the physician of ordinary skill. Parenteral administration may be performed by subcutaneous, intramuscular, intra-peritoneal or intravenous injection of a dosage form into the body by means of a sterile syringe, optionally a pen-like syringe or some other mechanical device such as an infusion pump. A further option is a composition which may be a powder or a liquid for the administration in the form of a nasal or pulmonary spray. As a still further option, the administration may be transdermally, e.g. from a patch. Compositions suitable for oral, buccal, rectal and vaginal administration may also be provided. The oral route of administration is preferred for compounds used in the present invention which are orally effective.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

In these Examples Haematology and serum chemistry including glucose were measured using an auto analyser (Vitros). Serum FSH was measured by IRMA (Coat-A-Count®, DPC, Los Angeles, Calif.). Serum C-telopeptide fragments of collagen type I degradation (S-CTX) were measured by ELISA, serum CrossLaps™ assay (Osteometer BioTech A/S—Denmark). Serum osteocalcin was determined by ELISA, an assay which determines the N-terminal mid segment of the molecule. Serum insulin and c-peptide were both assessed by RIA (Coat-A-Count® for insulin and Double Antibody C-peptide for c-peptide both DPC, Los Angeles, Calif.).

Example 1

Effect on GLP-1, GIP and Bone Resorption Rate of Oral Fructose 12 healthy women and men between 30–45, respectively 30–60, were included in a randomised, controlled cross over study comparing the effects of oral fructose on GLP-1, on GIP and on bone turnover. The individuals had not suffered diseases suspected to affect bone turnover such as cancer, rheumatoid arthritis or diseases compromising absorption from the gut or excretion/re-absorption from the kidney nor had they a history of serious diseases, which might influence the conduct of the study. A general laboratory screening including haematology and serum chemistry gave no indication of specific organ dysfunction. The individuals were not under influence of bone active medication, thus more than 3 months had passed since previous treatment with calcium, vitamin D, oestrogen or progestin in any administration form and the individuals had never been treated with bisphosphonates or fluoride.

Sampling

After fasting from 10 p.m. the evening prior to an experiment, blood samples were collected between 7:30 a.m. and 8:30 a.m. Immediately thereafter oral fructose were initiated. At precisely 1, 2, 3, 6 and 9 hours after the first blood sample, blood samples were collected. A washout period of 2 weeks was instituted between each experiment.

Interventions

Oral fructose consisted of 75 g fructose dissolved in 300 ml water with juice of a half lemon added.

Oral fructose induced a reduction of 36% in S-CT-X after 2 hours (FIG. 1A) whereas the occurrence of GLP-1 was doubled to the level of 220% after 2 hours compared to the baseline of 100% at To. The fragment of GLP-1 is one fragment of the major proglucagon fragment which is cleaved and activated in the intestine. According, the occurrence of the other parts or fragments are doubled to a similar level as GLP-1 and therefore can take part in the association of the reduction in S-CTX. The level of GIP was almost maintained at the baseline.

Example 2

Effect on GLP-1. GIP and Bone Resorption Rate of Oral Long Chained Fatty Acids, LCFA 12 healthy women and men between 30–45, respectively 30–60, with the same in- and exclusion criteria as in Example 1 were included in a randomised, controlled cross over study comparing the effects of oral long chained fatty acids on GLP-1, on GIP and on bone turnover.

Sampling

After fasting from 10 p.m. the evening prior to an experiment, blood samples were collected between 7:30 a.m. and 8:30 a.m. Immediately thereafter oral long chained fatty acids were initiated. At precisely 30 min, 1, 2, 3, 6 and 9 hours after the first blood sample, blood samples were collected. A washout period of 2 weeks was instituted between each experiment.

Interventions

Oral long chained fatty acids consisted of 70 ml emulsion of long chained fatty acids (Calogen).

Oral LCFA induced a reduction of 37% in S-CTX after 3 hours (FIG. 1B) and the occurrence of GLP-1 was doubled to the level of 230% after 3 hours compared to the baseline of 100% at To. These results are very similar to the equivalent data of Example 1. However, the occurrence of GIP was increased significantly to the level of 400%. Comparison with the almost maintained level of GIP in Example 1, indicating that GIP has no or very little influence on bone resorption.

Example 3

Effect on GLP-2, GIP and Bone Resorption Rate of Oral Protein 12 healthy women and men between 30–45, respectively 30–60, with the same in—and exclusion criteria as in Example 1 were included in a randomised, controlled cross over study comparing the effects of oral protein on GLP-2, on GIP and on bone turnover.

Sampling

After fasting from 10 p.m. the evening prior to an experiment, blood samples were collected between 7:30 a.m. and 8:30 a.m. Immediately thereafter oral protein were initiated. At precisely 30 min, 1, 2, 3, 6 and 9 hours after the first blood sample, blood samples were collected. A washout period of 2 weeks was instituted between each experiment.

Interventions

Oral protein consisted of 40 g. protein powder (Casilan) dissolved in 600 ml water.

Figure 1C:
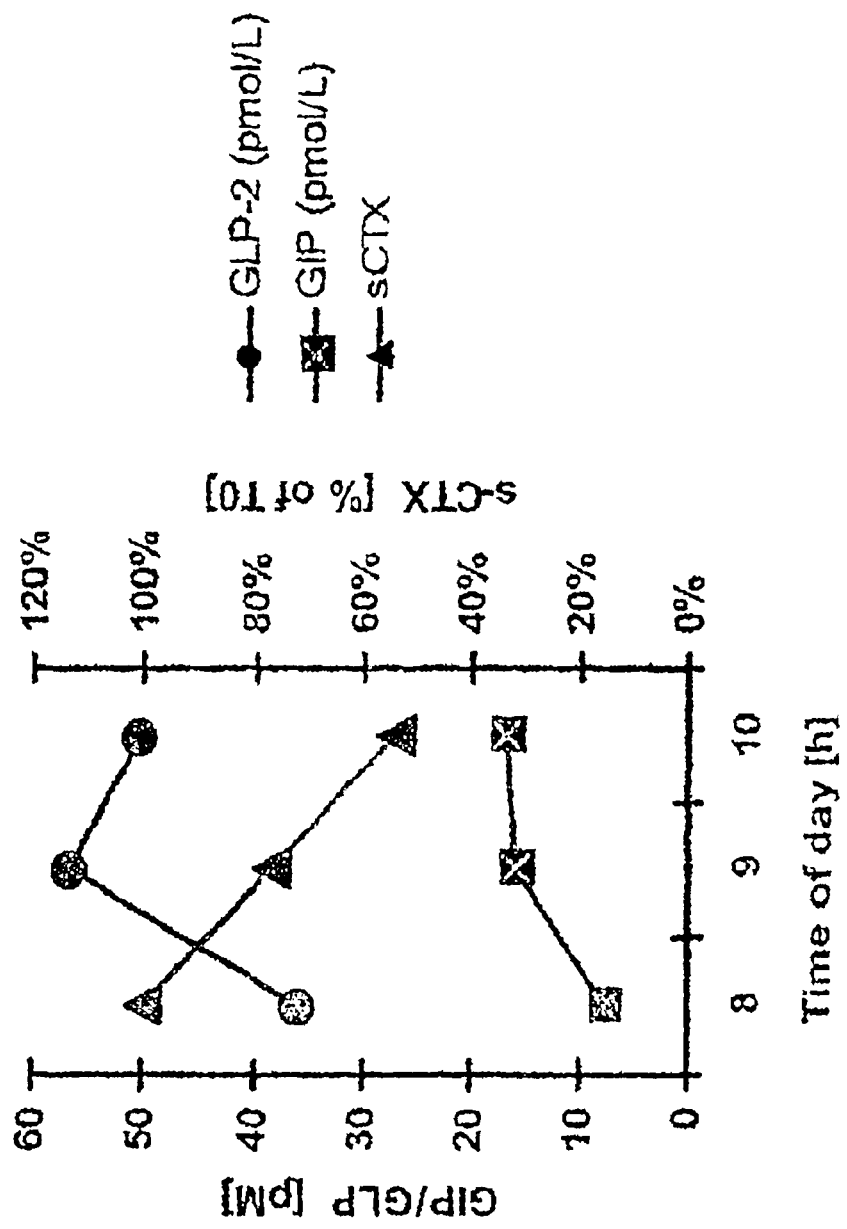
FIG. 1C shows the levels of GLP-2, GIP and S-CTX over a 2–3 hours period responding to oral protein.

Oral protein induced a reduction of 45% in S-CTX after 2 hours (FIG. 1C) whereas the occurrence of GLP-2 and GIP were both increased. The level of GIP was increased from 8 pM to 17 pM and the occurrence of GLP-2 was increased from 36 pM to 57 pM after 1 hour decrease slightly after 2 hours to the level of 51 pM. These results give reason to the similar conclusion as in Example 2.

Example 4

Effect of GLP-1, GLP-2 and Bone Resorption Rate of a Normal Mixed Meal 7 short bowel patients (<140 cm remnant small bowel) were recruited. 4 females and 3 male were studied comparing the effects of a normal mixed meal on GLP-1, on GLP-2 and on bone turnover.

The methodology of the measurement of GLP-1 and GLP-2 and the description of the test persons was as described in detail in Jeppesen, P. B. et al., Gut 2000; 47 (3):370–376.

Sampling

After an overnight fast prior to the admission peripheral venous blood was collected 15 minute before the test meal and 10, 20, 30, 45, 60, 120 and 180 minutes after the start of the meal, which was completed in 15 minutes.

Interventions

The normal mixed meal consisted of rye bread, toast, butter, cheese, jam, yoghurt, banana, and orange juice (total weight 755 g), with an energy content of 3.92 MJ and a protein:carbohydrate:fat energy ratio of 10%:52%:37% evaluated from food tables.

Figure 2:
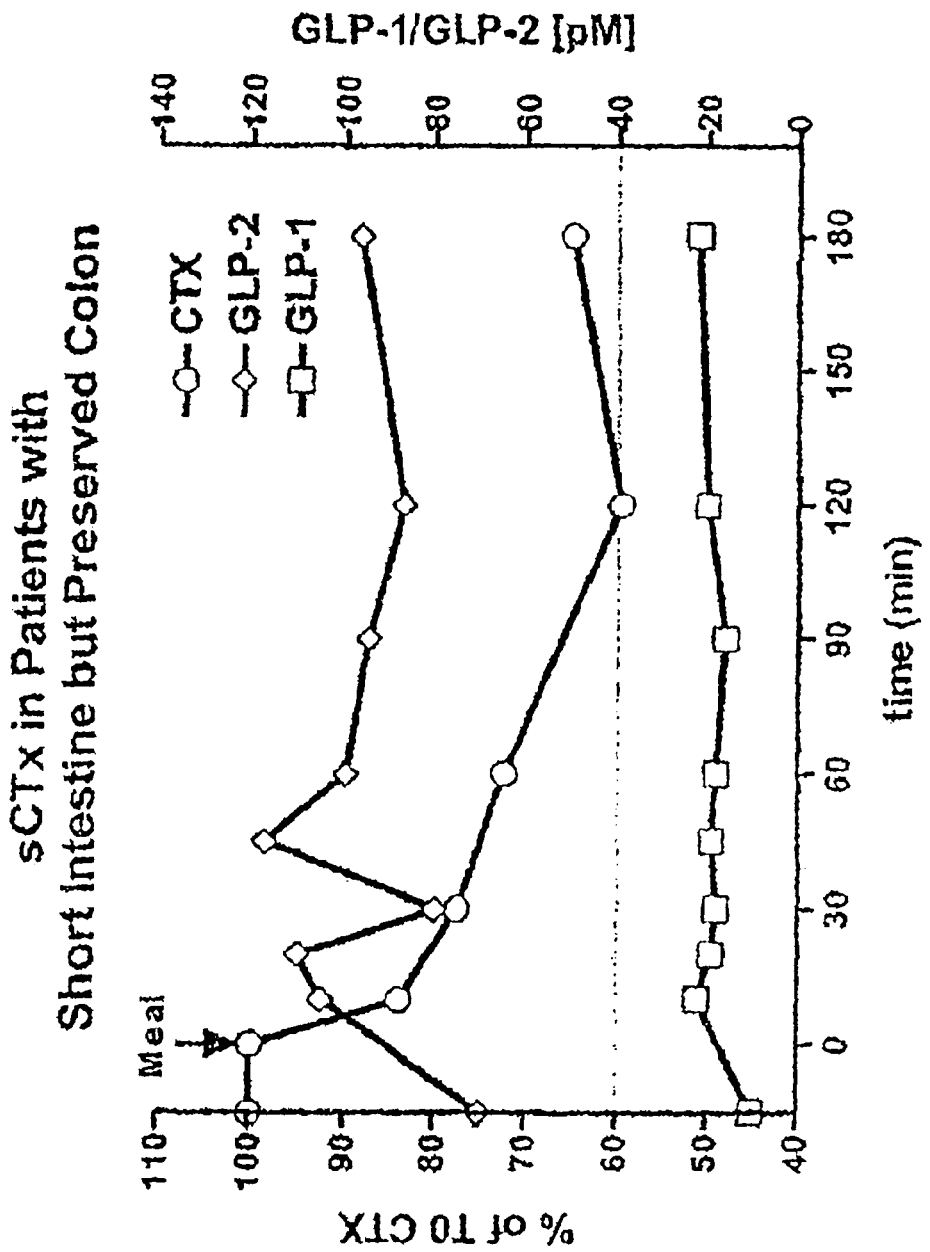
FIG. 2 shows results obtained in Example 4. The figure shows the levels of S-CTX, GLP-1 and GLP-2 in patients with short intestine but preserved colon over a 3 hours period responding to a normal meal.
Figure 3:
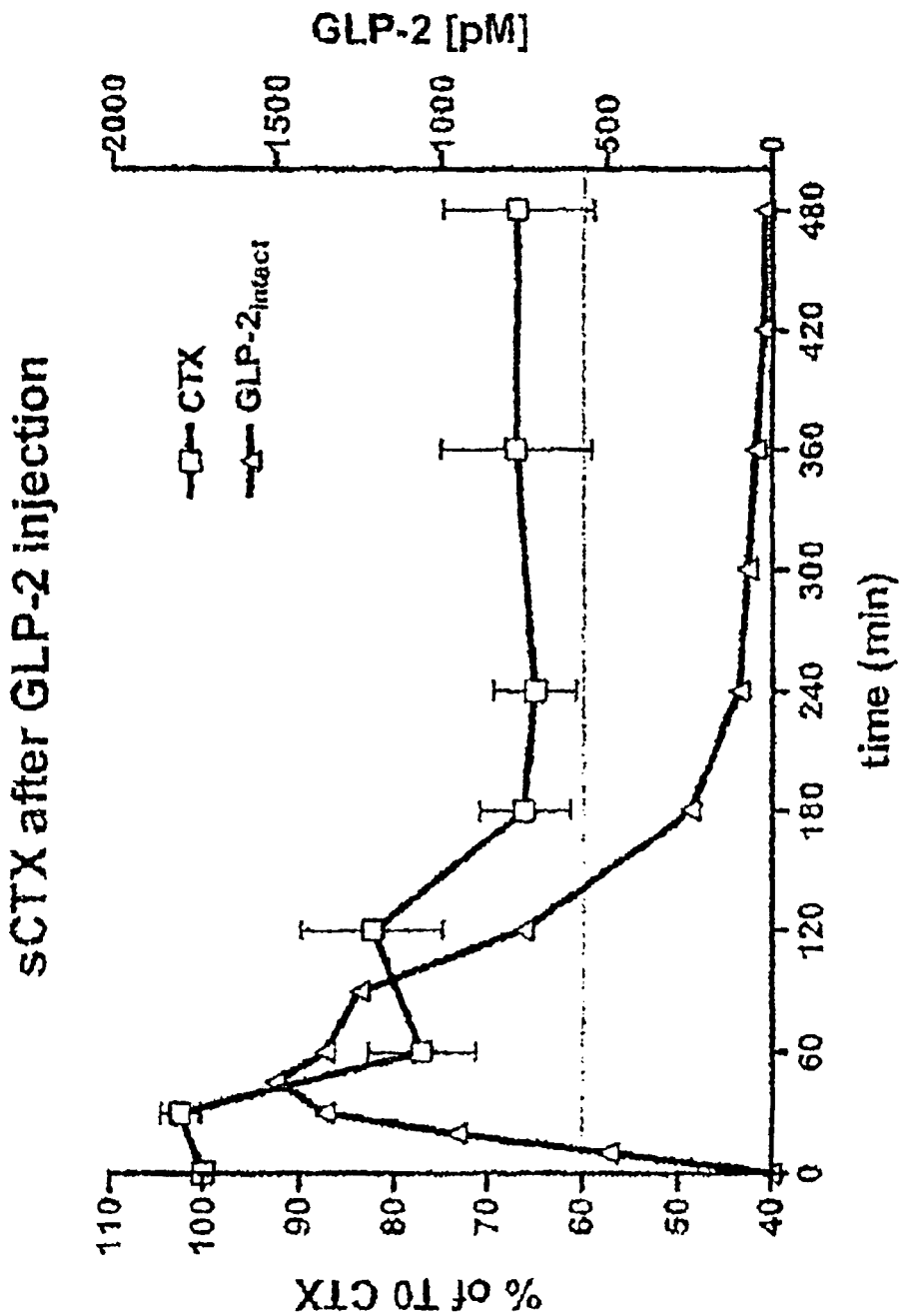
FIG. 3 shows results obtained in Example 5. The figure shows the levels of S-CTX and GLP-2intact over a 7 hours period responding to a GLP-2 injection.

A normal mixed meal induced a reduction of 40% in S-CTX after 2 hours (FIG. 2) whereas the occurrence of GLP-1 and GLP-2 were both increased. The level of GLP-1 was increased from 70 pM to 98 pM after 3 hours and the occurrence of GLP-2 was increased from 10 pM to 22 pM after 3 hours. These results indicate that GLP-1 and/or GLP-2 can take part in the association of the reduction in S-CTX.

Example 5

Effect on GLP-$2_{intact}$ and Bone Resorption Rate of a GLP-2 Injection 6 healthy women and 3 healthy men between 24–53 were included in a study comparing the effect of a GLP-2 injection on GLP-$2_{intact}$ and on bone turnover.

The description of the methodology of measurement of GLP-$2_{intact}$ and total GLP-2 and the description of the test persons was as described in detail in Hartmann, B. et al., J Clin Endocrinol Metab 2000; 85 (8):2884–2888.

Sampling

Blood samples were drawn at regular intervals before, during, and after the injection.

Interventions

The test persons received a subcutaneous bolus injection of 400 µg synthetic human GLP-2.

The GLP-2 injection induced a reduction of 33% in S-CTX after 3 hours whereas the level of GLP-2 increased naturally after the injection to a peak after 1 hour indicating the association between GLP-2 and the reduction in S-CTX.

The invention has been described in detail with reference to preferred embodiments thereof. However, it will be appreciated that those skilled in the art, upon consideration of the disclosure, may make modification and improvements within the spirit and scope of the invention. All references disclosed herein are incorporated herein by reference.

What is claimed is:

1. A method of inhibiting bone resorption and/or promoting bone formation, comprising,
   identifying a subject at risk of developing a disease wherein bone resorption, insufficient bone formation or both is a factor, wherein the identification step comprises assessing the level of bone resorption or formation in the subject by biochemical assessment of biochemical markers,
   administering to the subject a compound selected from the group consisting of GLP-2, GLP-2 analogues capable of binding and activating a GLP-2 receptor, agonists of the GLP-2 receptor, and pharmaceutically acceptable salts, esters or amides of any of the foregoing; and
   inhibiting the bone resorption, promoting bone formation, or both in the subject.

2. The method of claim 1 wherein the composition is selected from the group consisting of GLP-2, GLP-2 analogues, and pharmaceutically acceptable salts, esters or amides thereof.

3. The method of claim 1 wherein the composition is administered orally.

4. A method of prophylactically treating a subject at risk of developing a disease wherein bone resorption and/or insufficient bone formation is a factor, the method comprising the steps of
   a) identifying a subject at risk of developing such a disease wherein the identification step comprises assessing the level of bone resorption or formation in the subject by biochemical assessment of biochemical markers; and
   b) administering to the subject an amount of a compound selected from the group consisting of GLP-2, GLP-2 analogues capable of binding and activating a GLP-2 receptor, agonists of the GLP-2 receptor, and pharmaceutically acceptable salts of any of the foregoing, effective to inhibit onset of said disease.

5. A method according to claim 1, wherein the disease wherein bone resorption or insufficient bone formation is a factor, is selected from hyperparathyroidism, Paget's disease, hypercalcemia of malignancy, osteolytic lesions produced by bone metastasis, bone loss due to immobilisation or sex hormone deficiency, osteomalacia, hyperostosis and osteopetrosis.

6. A method according to claim 1 wherein the disease wherein bone resorption or insufficient bone formation is a factor, is osteoporosis.

7. A method according to claim 1, wherein the subject is a human.

8. A method of therapeutic or prophylactic treatment of a disease wherein bone resorption or insufficient bone formation is a factor, comprising:
   identification of a patient at risk of developing a disease wherein bone resorption, insufficient bone formation or both is a factor, wherein the identification step comprises an assessment of the level of bone resorption or formation in the patient by biochemical assessment of biochemical markers, administration to the patient of a composition comprising a compound selected from the group consisting of GLP-2, GLP-2 analogues capable of binding and activating a GLP-2 receptor, agonists of the GLP-2 receptor, and pharmaceutically acceptable salts, esters or amides thereof; and inhibiting the bone resorption, or promoting bone formation, or both in the patient.

9. The method of claim 8, wherein the disease is selected from hyperparathyroidism, Paget's disease, hypercalcemia of malignancy, osteolytic lesions produced by bone metastasis, bone loss due to immobilisation or sex hormone deficiency, osteomalacia, hyperostosis and osteopetrosis.

10. The method of any one of claim 1, 4, or 8, wherein the identification step comprises measuring the level of the biochemical marker: serum C-telopeptide fragment of collagen Type I.

11. The method of any one of claim 1, 4, or 8, wherein the identification step further comprises measuring the level of one or more of the following biochemical markers: serum C-telopeptide fragment of Collagen Type I.

12. The method of claim 10, wherein the identification step further comprises comparing the level of one or more of the markers to a baseline control, thereby assessing the level of bone resorption and formation in the subject or patient.

13. The method of claim 11 wherein the identification step further comprises comparing the level of one or more of the markers to a baseline control, thereby assessing the level of bone resorption and formation in the subject or patient.

14. The method of any one of claim 1, 4, or 8, further comprising monitoring changes in the level of bone resorption in the subject or patient following said administration.

15. A method of claim 1, wherein a GLP-2 analogue is a derivative of GLP-2.

16. A method of claim 15 wherein the derivative of GLP-2 is selected from the group consisting of acid addition salts, carboxylate salts, lower alkyl esters, lower alkyl amides of GLP-2 and chemically modified GLP-2 peptides which retain the bone resorption decreasing and/or bone formation increasing properties of GLP-2 at an equivalent or increased level.

17. A method of claim 2 wherein a GLP-2 analogue is a derivative of GLP-2.

18. A method of claim 17 wherein the derivative of GLP-2 is selected from the group consisting of acid addition salts, carboxylate salts, lower alkyl esters, lower alkyl amides of GLP-2 and chemically modified GLP-2 peptides which retain the bone resorption decreasing and/or bone formation increasing properties of GLP-2 at an equivalent or increased level.

19. A method of claim 4 wherein a GLP-2 analogue is a derivative of GLP-2.

20. A method of claim 19 wherein the derivative of GLP-2 is selected from the group consisting of acid addition salts, carboxylate salts, lower alkyl esters, lower alkyl amides of GLP-2 and chemically modified GLP-2 peptides which retain the bone resorption decreasing and/or bone formation increasing properties of GLP-2 at an equivalent or increased level.

21. A method of claim 8 wherein a GLP-2 analogue is a derivative of GLP-2.

22. A method of claim 21 wherein the derivative of GLP-2 is selected from the group consisting of acid addition salts, carboxylate salts, lower alkyl esters, lower alkyl amides of GLP-2 and chemically modified GLP-2 peptides which retain the bone resorption decreasing and/or bone formation increasing properties of GLP-2 at an equivalent or increased level.

* * * * *